US012276647B2

(12) United States Patent
Yu et al.

(10) Patent No.: US 12,276,647 B2
(45) Date of Patent: Apr. 15, 2025

(54) ENVIRONMENTAL MONITORING DEVICE FOR AIR POLLUTION (71) Applicant: Shandong Normal University, Jinan (CN)

(72) Inventors: Guanliu Yu, Jinan (CN); Huapeng Zhang, Jinan (CN)

(73) Assignee: Shandong Normal University, Jinan (CN)

( * ) Notice: Subject to any disclaimer, the term of this patent is extended or adjusted under 35 U.S.C. 154(b) by 0 days.

(21) Appl. No.: 18/885,944

(22) Filed: Sep. 16, 2024

(65) Prior Publication Data
US 2025/0003935 A1 Jan. 2, 2025

(30) Foreign Application Priority Data

Mar. 26, 2024 (CN) .......................... 202410345783.0

(51) Int. Cl.
*G01N 33/00* (2006.01)
*G01N 1/22* (2006.01)
*G01N 1/24* (2006.01)
*G01N 1/26* (2006.01)

(52) U.S. Cl.
CPC ....... *G01N 33/0029* (2013.01); *G01N 1/2273* (2013.01); *G01N 1/24* (2013.01); *G01N 1/26* (2013.01); *G01N 2001/245* (2013.01)

(58) Field of Classification Search
USPC ......... 73/31.01, 31.02, 31.03, 31.05, 863.45, 73/863.56
See application file for complete search history.

(56) References Cited

U.S. PATENT DOCUMENTS

| 5,404,763 | A | * | 4/1995 | Guggenheim | ........... G01N 1/26 73/863.31 |
| 5,691,487 | A | * | 11/1997 | Green | ...................... G01N 1/26 73/864.91 |
| 6,114,964 | A | * | 9/2000 | Fasano | ............... G01N 33/0075 340/628 |

(Continued)

FOREIGN PATENT DOCUMENTS

JP 10148680 * 6/1998 ......... G01N 33/0004

OTHER PUBLICATIONS

CNIPA, Notification to grant patent right for Chinese application CN202410345783.0, May 9, 2024.

*Primary Examiner* — Daniel S Larkin
(74) *Attorney, Agent, or Firm* — Hemisphere Law, PLLC; Zhigang Ma (57) ABSTRACT The present invention belongs to the technical field of environmental monitoring, in particular to an environmental monitoring device for air pollution, comprising a monitoring frame, a monitoring shell arranged on a top end of the monitoring frame and an environmental monitor fixedly installed inside the monitoring shell through a connecting plate. An air sampling assembly is installed inside the environmental monitor; the air sampling assembly comprises air intake covers, and an electric push rod, a rack I, a gear I, a spur gear, an internal gear, a rotating disk, limiting blocks, limiting rods, a cross limiting track, an L-shaped frame and a strip-shaped plate which are used for driving the air intake covers. A cleaning assembly is installed on the air sampling assembly.

6 Claims, 10 Drawing Sheets

(56) References Cited

U.S. PATENT DOCUMENTS

| | | | |
|---|---|---|---|
| 6,252,510 B1 * | 6/2001 | Dungan | G01N 33/0075 340/539.1 |
| 6,662,628 B2 * | 12/2003 | Horvath | B01L 7/02 73/29.01 |
| 2007/0085678 A1 | 4/2007 | Joy et al. | |
| 2014/0266682 A1 | 9/2014 | Gettings et al. | |
| 2023/0393030 A1 | 12/2023 | Pollitt et al. | |

* cited by examiner

ENVIRONMENTAL MONITORING DEVICE FOR AIR POLLUTION

TECHNICAL FIELD

The present invention belongs to the technical field of environmental monitoring, in particular to an environmental monitoring device for air pollution.

BACKGROUND

Environmental monitoring is to track the change of environmental quality and determine the level of environmental quality through the detection of the content and emissions of various substances that have an impact on human beings and the environment, so as to provide a basis and guarantee for environmental management, pollution control and other work. In short, environmental monitoring is a precondition for carrying out all environmental work. Environmental monitoring generally includes background investigation to determine programs, layout optimization, on-site sampling, sample transportation, experimental analysis, data collection, analysis and synthesis, etc. In general, environmental monitoring is a process of obtaining information by planning, sampling, analysis and synthesis.

At present, an air monitor is fixedly installed in a device, and generally monitors an external gas environment only through air intake holes that face one direction. Due to the random change of wind direction, the accuracy of the gas environment monitoring under the leeward condition will be greatly reduced, thereby affecting the concentration of contents in the collected air. Meanwhile, the monitoring efficiency is low due to the slow flow of the gas. Moreover, the air intake holes are exposed for a long time, and are easily invaded by rain, thereby affecting the service life of electronic elements, reducing the use effect of the device and being difficult to meet the actual use needs.

In order to solve the above problems, the present application provides an environmental monitoring device for air pollution.

SUMMARY

The present invention provides an environmental monitoring device for air pollution, which can effectively solve the problems raised in the background.

To achieve the above purpose, the present invention provides the following technical solution: an environmental monitoring device for air pollution comprises a monitoring frame, a monitoring shell arranged on a top end of the monitoring frame and an environmental monitor fixedly installed inside the monitoring shell through a connecting plate.

An air sampling assembly is installed inside the environmental monitor; the air sampling assembly comprises air intake covers, and an electric push rod, a first rack, a first gear, a spur gear, an internal gear, a rotating disk, limiting blocks, limiting rods, a cross-limiting track, an L-shaped frame and a strip-shaped plate which are used for driving the air intake covers; the cross-limiting track is fixed inside the monitoring shell; the rotating disk is rotatably connected to a center of an upper surface of the cross-limiting track through a rotating shaft; four groups of limiting blocks arranged annularly and equidistantly are slidably connected inside the cross-limiting track; the limiting rods are fixed on upper surfaces of the limiting blocks; a surface of the rotating disk is provided with limiting grooves adapted with the limiting rods; the internal gear is fixed to an upper surface of the rotating disk; an inner side of the internal gear is engaged with the spur gear; the rotating shaft is fixed at an inner center of the spur gear through a screw; the first gear is fixed to the surface of the rotating shaft; a surface of the first gear is engaged with the first rack; the strip-shaped plate is fixed to an inner side wall of the monitoring shell; an upper surface of the strip-shaped plate is connected with the electric push rod through a bolt; a top end of the rotating shaft is rotatably connected with the strip-shaped plate through a bearing; the L-shaped frame is fixed to one side of the limiting blocks; the air intake cover is fixed to one end of the L-shaped frame; and both sides of a surface of the air intake cover are provided with air intake holes arranged symmetrically.

A cleaning assembly is installed on the air sampling assembly; the cleaning assembly comprises a cleaning rod for cleaning dust off a filter screen, second racks, second gears, a chain mechanism and a fixing plate; the symmetrically arranged second racks are fixed to both sides of the air intake cover; surfaces of the second racks are engaged with the second gears; a first rotating rod is installed inside the second gears through a screw; the chain mechanism rotates on a top end of the first rotating rod; a second rotating rod rotates on one end of the chain mechanism; the cleaning rod is fixed to a bottom end of the second rotating rod; and the fixing plate is fixed to one side of a surface of the monitoring shell near the cleaning rod;

An exhaust assembly is installed inside the monitoring shell; the exhaust assembly comprises exhaust fans for exhaust, sealing plates, limiting pins, a U-shaped frame, a first and second magnets; round holes are arranged at bottom four corners of the monitoring shell; the exhaust fans are arranged in the round holes; two groups of symmetrically arranged sealing plates are installed inside the monitoring shell; limiting pins are slidably connected inside the sealing plates respectively; the U-shaped frame is fixed to upper surfaces of two groups of the sealing plates respectively; the first magnet is fixed to an upper surface of the U-shaped frame; bottoms of four groups of the air intake covers are provided with rectangular grooves; and the second magnets are arranged in the rectangular grooves.

As a preferred environmental monitoring device for air pollution in the present invention, the surface of the monitoring shell is provided with a moving groove adapted with each air intake cover, and each air intake cover and the monitoring shell are slidably connected through the moving groove.

As a preferred environmental monitoring device for air pollution in the present invention, two groups of air baffle plates arranged symmetrically are fixed inside each air intake cover.

As a preferred environmental monitoring device for air pollution in the present invention, a plurality of groups of diversion grooves arranged equidistantly are arranged on both sides of each air intake cover.

As a preferred environmental monitoring device for air pollution in the present invention, two groups of baffle plates arranged symmetrically are fixed to one side of each air intake cover, and a supporting plate is connected inside the monitoring shell through a bolt.

As a preferred environmental monitoring device for air pollution in the present invention, the air intake holes of the air intake covers are fixedly connected with filter screens through screws.

As a preferred environmental monitoring device for air pollution in the present invention, a spring is wound on the surface of each limiting pin.

Compared with the prior art, the present invention has the following beneficial effects:

The air sampling assembly is arranged; through the combined use of the air intake covers, the electric push rod, the first rack, the first gear, the spur gear, the internal gear, the rotating disk, the limiting blocks, the limiting rods, the cross-limiting track, the L-shaped frame and the strip-shaped plate, on the one hand, the monitoring range can be increased and the accuracy of environmental monitoring can be improved; and on the other hand, the accuracy of environmental monitoring is not reduced by the random change of the wind direction to avoid affecting the concentration of contents in the collected air, and meanwhile, the flow of the gas is not affected, so that the environmental pollution monitoring efficiency is higher. Moreover, the electric push rod is started for resetting and driving each air intake cover to move into the monitoring shell near the position of the filter screen to avoid air entry. Through the extension and contraction of each air intake cover regularly, air is sampled, so as to prevent rainwater from intruding into the monitoring shell and avoid affecting the service life of the electronic elements of the environmental monitor, thereby improving the use effect of the device and satisfying the actual use needs.

The wind direction is partially blocked through the baffle plate, and discharged to the position of the filter screen along the diversion grooves. The diversion grooves can help to guide the flow of wind and improve the collection efficiency of wind energy. Meanwhile, the air can effectively reduce air impurities through the filter screen, thereby improving the accuracy of environmental monitoring data and further improving the use effect of the device. The air baffle plates can increase the flow of the air and increase the entry of the air, to avoid air overflow, thereby further improving the use effect of the device and improving the monitoring effect.

The cleaning assembly is arranged. Through the combined use of the cleaning rod, the second racks, the second gears, the chain mechanism and the fixing plate, the impurities and dust on the surface of the filter screen can be cleaned up through the cleaning rod to avoid blocking the filter holes of the filter screen by the dust and the impurities, thereby improving the smoothness of air entry, further improving the accuracy of air pollution monitoring data and ensuring the normal operation of the device. The structure is more flexible to use, thereby satisfying the actual use needs. On the other hand, the end grooves of the diversion grooves can be cleaned to avoid blocking the ends of the diversion grooves, so as to improve the air intake effect.

The exhaust assembly is arranged. Through the combined use of the exhaust fans, the sealing plates, the limiting pins, the U-shaped frame, the first magnet and the second magnets, the air that remains inside the monitoring shell is regularly discharged and new air is introduced, which can ensure that each detection is based on fresh air samples, thereby improving the accuracy and the reliability of the data. At the same time, by regularly discharging the residual air and introducing the new air, the dust accumulation inside the device can be reduced, and the risk of device failure can be reduced; and by regularly replacing the air samples, the wear inside the device can be slowed, thereby prolonging the service life of the device.

DESCRIPTION OF DRAWINGS

The drawings are used to provide further understanding for the present invention and constitute part of the description. The drawings are used to explain the present invention together with the embodiments of the present invention, and do not constitute a limitation to the present invention. In the drawings.

In the drawings: 1, monitoring frame; 2, monitoring shell; 3, environmental monitor; 4, air sampling assembly; 401, electric push rod; 402, first rack; 403, first gear; 404, spur gear; 405, internal gear; 406, rotating disk; 407, limiting block; 408, limiting rod; 409, cross-limiting track; 410, L-shaped frame; 411, air intake cover; 412, air baffle plate; 413, diversion groove; 414, baffle plate; 415, supporting plate; 416, filter screen; 417, strip-shaped plate; 5, cleaning assembly; 501, second rack; 502, second gear; 503, chain mechanism; 504, fixing plate; 505, cleaning rod; 6, exhaust assembly; 601, exhaust fan; 602, sealing plate; 603, limiting pin; 604, spring; 605, U-shaped frame; 606, first magnet; 607, second magnet.

DETAILED DESCRIPTION

The technical solutions in the embodiments of the present invention will be clearly and fully described below in combination with the drawings in the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiments: As shown in FIGS. 1-10, an environmental monitoring device for air pollution comprises a monitoring frame 1, a monitoring shell 2 arranged on a top end of the monitoring frame 1 and an environmental monitor 3 fixedly installed inside the monitoring shell 2 through a connecting plate.

Figure 1:
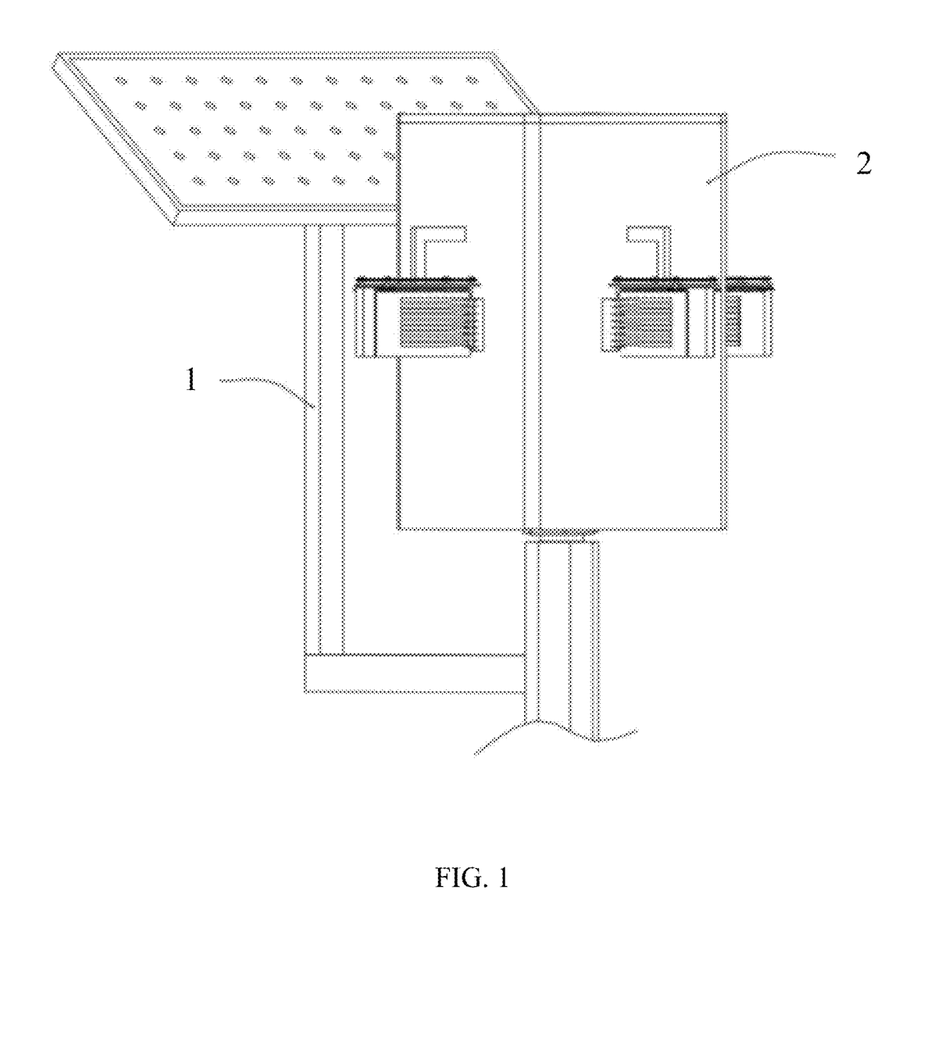
FIG. 1 is an overall structural schematic diagram of the present invention.
Figure 2:
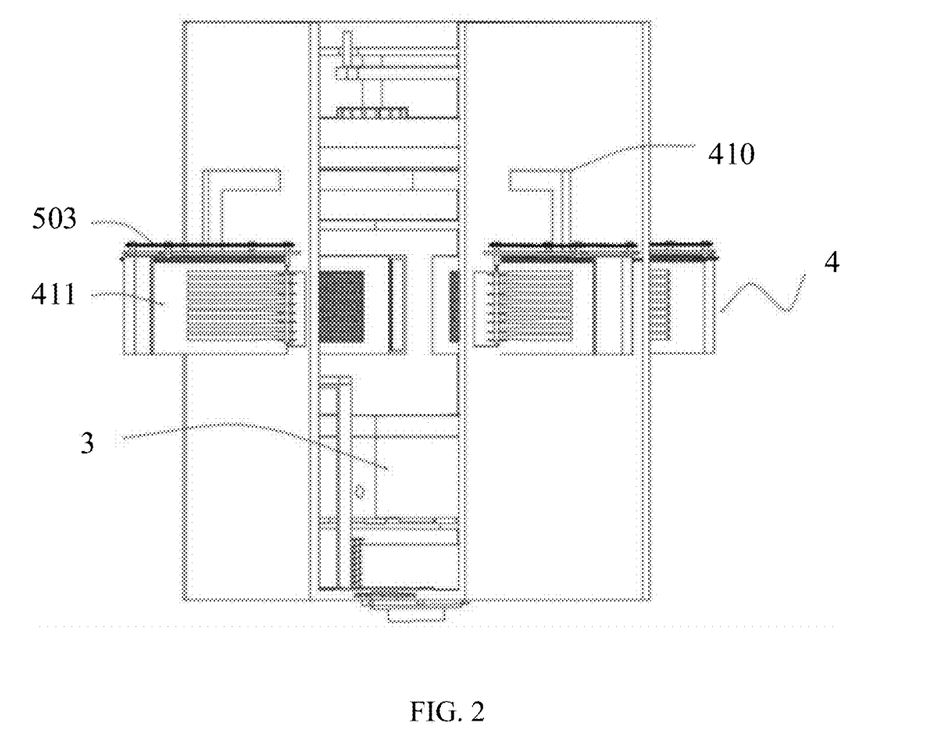
FIG. 2 is a local structural sectional view of a monitoring shell in the present invention.
Figure 3:
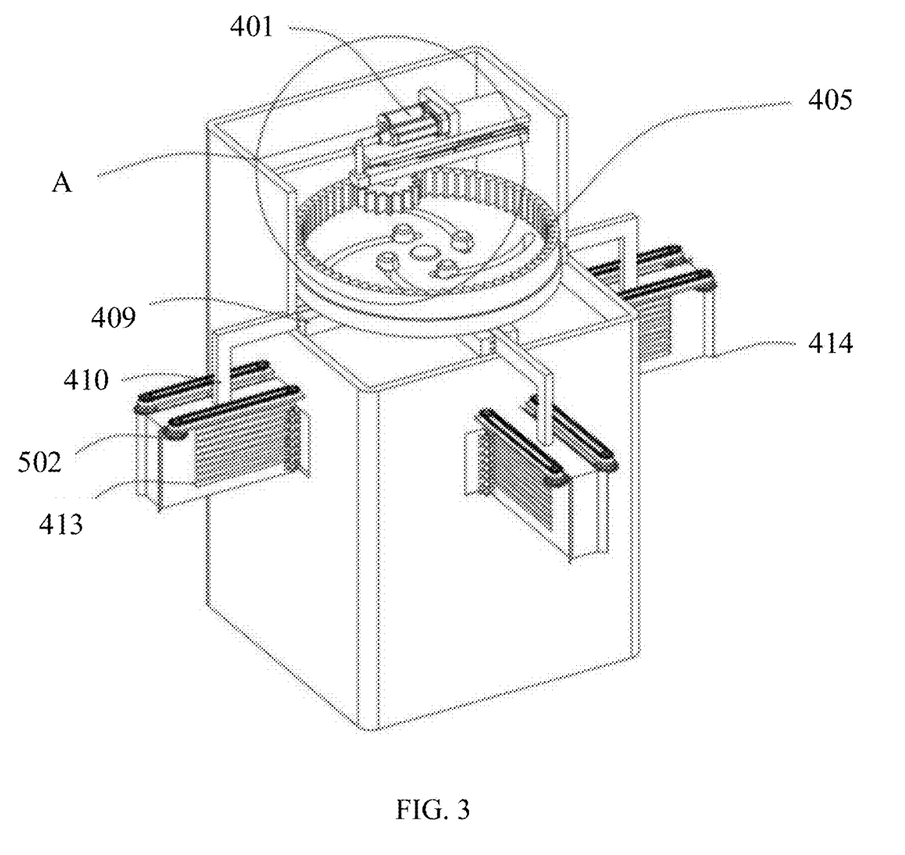
FIG. 3 is a structural schematic diagram of connecting parts such as an internal gear and a rotating disk in the present invention.
Figure 4:
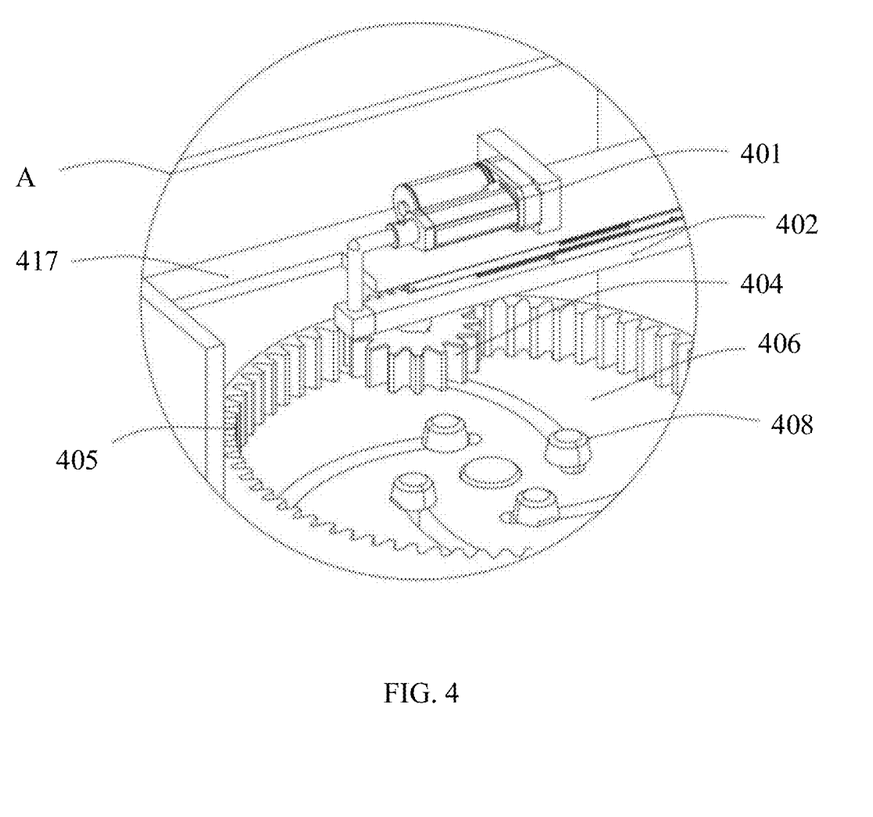
FIG. 4 is a schematic diagram of an enlarged structure at A of FIG. 3 in the present invention.
Figure 5:
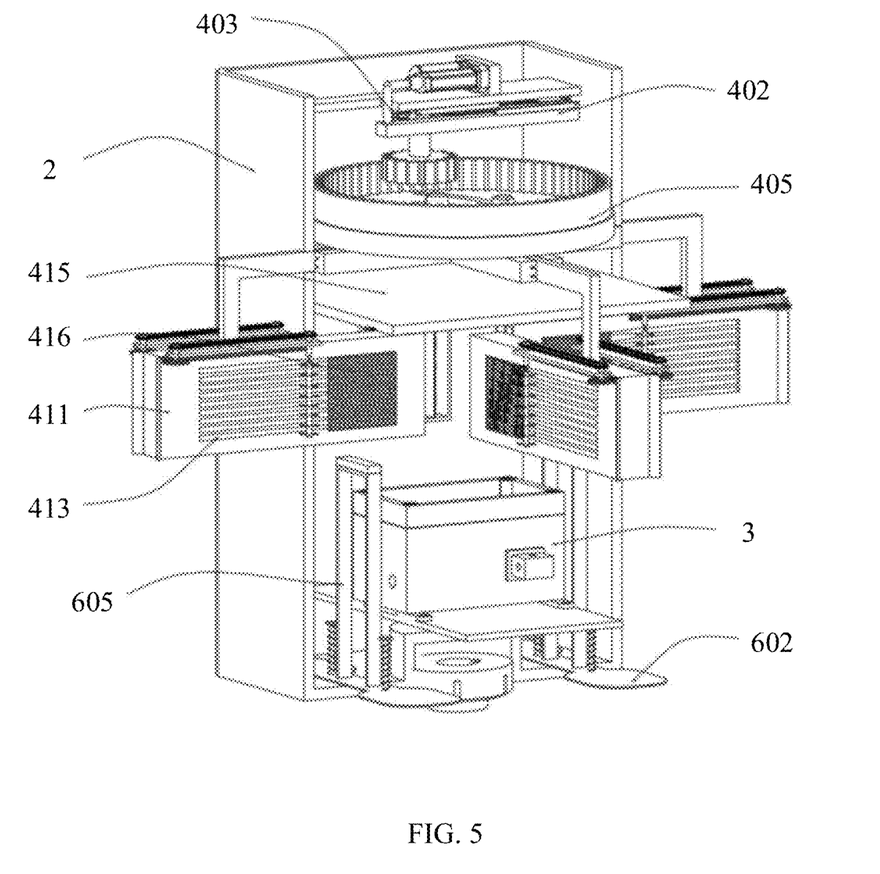
FIG. 5 is a structural sectional view of a monitoring shell in the present invention.

An air sampling assembly 4 is installed inside the environmental monitor 3; the air sampling assembly 4 comprises air intake covers 411, and an electric push rod 401, a first rack 402, a first gear 403, a spur gear 404, an internal gear 405, a rotating disk 406, limiting blocks 407, limiting rods 408, a cross-limiting track 409, an L-shaped frame 410, air baffle plates 412, diversion grooves 413, baffle plates 414, a supporting plate 415, a filter screen 416 and a strip-shaped plate 417, all of which are used for driving the air intake covers 411.

The cross-limiting track 409 is fixed inside the monitoring shell 2; the rotating disk 406 is rotatably connected to a center of an upper surface of the cross-limiting track 409 through a rotating shaft; four groups of limiting blocks 407 arranged annularly and equidistantly are slidably connected inside the cross-limiting track 409; the limiting rods 408 are fixed on upper surfaces of the limiting blocks 407; a surface of the rotating disk 406 is provided with limiting grooves adapted with the limiting rods 408; the limiting rods 408 and the rotating disk 406 are slidably connected through the limiting grooves; the internal gear 405 is fixed to an upper surface of the rotating disk 406; an inner side of the internal gear 405 is engaged with the spur gear 404; the rotating shaft is fixed at an inner center of the spur gear 404 through a screw; the first gear 403 is fixed to the surface of the rotating shaft; a surface of the first gear 403 is engaged with the first rack 402; the strip-shaped plate 417 is fixed to an inner side wall of the monitoring shell 2; the first rack 402 is slidably connected with the strip-shaped plate 417 through a sliding rail; an upper surface of the strip-shaped plate 417 is connected with the electric push rod 401 through a bolt; an output end of the electric push rod 401 is fixedly connected with the first rack 402 through an L-shaped rod; a top end of the rotating shaft is rotatably connected with the strip-shaped plate 417 through a bearing; the L-shaped frame 410 is fixed to one side of the limiting blocks 407; each air intake cover 411 is fixed to one end of the L-shaped frame 410; and both sides of a surface of each air intake cover 411 are provided with air intake holes arranged symmetrically. The surface of the monitoring shell 2 is provided with a moving groove adapted with each air intake cover 411, and each air intake cover 411 and the monitoring shell 2 are slidably connected through the moving groove. Two groups of air baffle plates 412 arranged symmetrically are fixed inside each air intake cover 411. A plurality of groups of diversion grooves 413 arranged equidistantly are arranged on both sides of each air intake cover 411. Two groups of baffle plates 414 arranged symmetrically are fixed to one side of each air intake cover 411, and a supporting plate 415 is connected inside the monitoring shell 2 through a bolt. The air intake holes of the air intake covers 411 are fixedly connected with filter screens 416 through screws.

Figure 6:
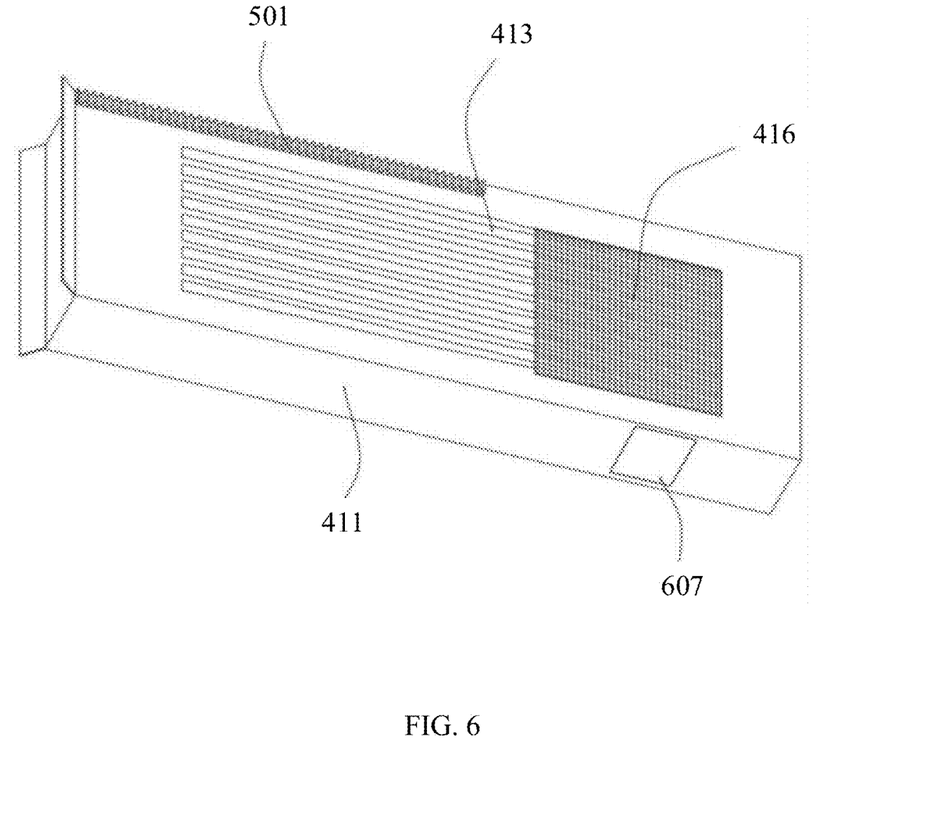
FIG. 6 is a structural schematic diagram of connecting parts such as an air intake cover and a second magnet in the present invention.

A cleaning assembly 5 is installed on the air sampling assembly 4; the cleaning assembly 5 comprises a cleaning rod 505 for cleaning dust off the filter screen 416, second racks 501, second gears 502, a chain mechanism 503 and a fixing plate 504.

The symmetrically arranged second racks 501 are fixed to both sides of each air intake cover 411; surfaces of the second racks 501 are engaged with the second gears 502; a first rotating rod is installed inside the second gears 502 through a screw; the chain mechanism 503 rotates on a top end of the first rotating rod; a second rotating rod rotates on one end of the chain mechanism 503; the cleaning rod 505 is fixed to a bottom end of the second rotating rod; the fixing plate 504 is fixed to one side of a surface of the monitoring shell 2 near the cleaning rod 505; and the fixing plate 504 is rotatably connected with the first rotating rod and the second rotating rod through bearings.

Figure 9:
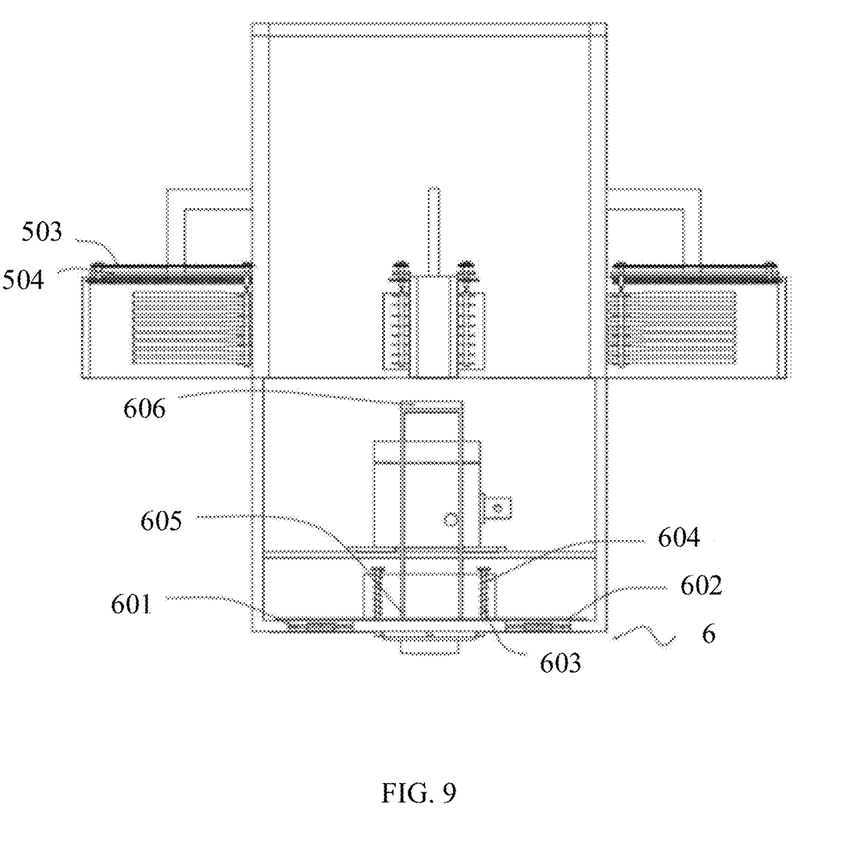
FIG. 9 is a structural schematic diagram of connecting parts such as an exhaust fan and a sealing plate in the present invention.
Figure 10:
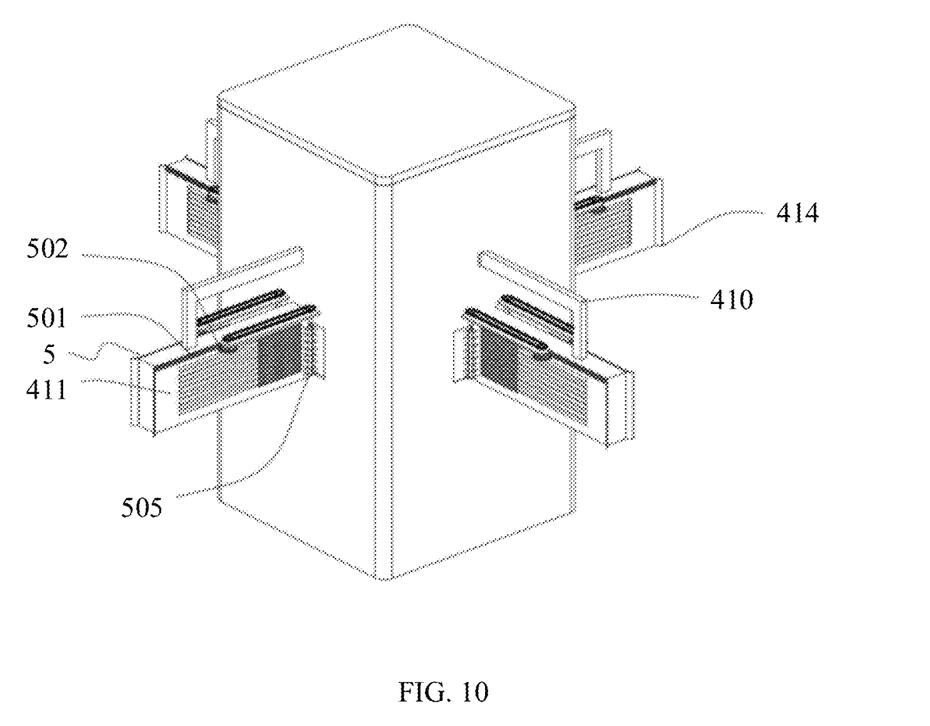
FIG. 10 is a structural schematic diagram of movement of an air intake cover in the present invention.

An exhaust assembly 6 is installed inside the monitoring shell 2; the exhaust assembly 6 comprises exhaust fans 601 for exhaust, sealing plates 602, limiting pins 603, springs 604, a U-shaped frame 605, a first magnet 606 and second magnets 607.

Round holes are arranged at bottom four corners of the monitoring shell 2; the exhaust fans 601 are arranged in the round holes; the exhaust fans 601 are fixedly connected with the monitoring shell 2 by bolts; two groups of symmetrically arranged sealing plates 602 are installed inside the monitoring shell 2; one group of sealing plates 602 corresponds to two groups of round holes; limiting pins 603 are slidably connected inside the sealing plates 602 respectively; the limiting pins 603 are fixedly connected with the monitoring shell 2; the springs 604 are wound on the surfaces of the limiting pins 603; both ends of the spring 604 are fixedly connected with the monitoring shell 2 and the limiting pins 603 respectively; the U-shaped frame 605 is fixed to upper surfaces of the two groups of sealing plates 602 respectively; the first magnet 606 is fixed to an upper surface of the U-shaped frame 605; bottoms of four groups of the air intake covers 411 are provided with rectangular grooves; the second magnet 607 are arranged in the rectangular grooves; and the second magnets 607 are fixedly connected with the air intake covers 411.

In the implementation solution, when the environmental monitoring device for air pollution needs to monitor a polluted environment, firstly, the electric push rod 401 is started to drive the first rack 402 to move. Because the first rack 402 and the first gear 403 are engaged, the first gear 403 is driven to rotate. Through the rotation of the first gear 403, the spur gear 404 is driven to rotate. Because the spur gear 404 is engaged with the internal gear 405, the internal gear 405 is driven to rotate. The internal gear 405 drives the rotating disk 406 to rotate synchronously. With the rotation of the rotating disk 406, the limiting rod 408 slides in the limiting groove formed in the rotating disk 406. Then, the limiting rod 408 drives the limiting block 407 to slide in the cross-limiting track 409. As the limiting block 407 slides and drives the L-shaped frame 410 to move, the L-shaped frame 410 drives each air intake cover 411 to constantly move out of the monitoring shell 2. After the four groups of air intake covers 411 extend from the monitoring shell 2, a fan structure is formed. When encountering wind, the wind blows the air intake covers 411. Thus, the air intake covers 411 drive the monitoring shell 2 to rotate in the monitoring frame 1, so that the air enters each air intake cover 411 through the air intake holes and is discharged into the monitoring shell 2 through the air intake covers 411. Through monitoring by the environmental monitor 3, on the one hand, the monitoring range can be increased and the accuracy of environmental monitoring can be improved while rotating; and on the other hand, the accuracy of environmental monitoring is not reduced by the random change of the wind direction to avoid affecting the concentration of contents in the collected air, and meanwhile, the flow of the gas is not affected, so that the environmental pollution monitoring efficiency is higher.

Figure 7:
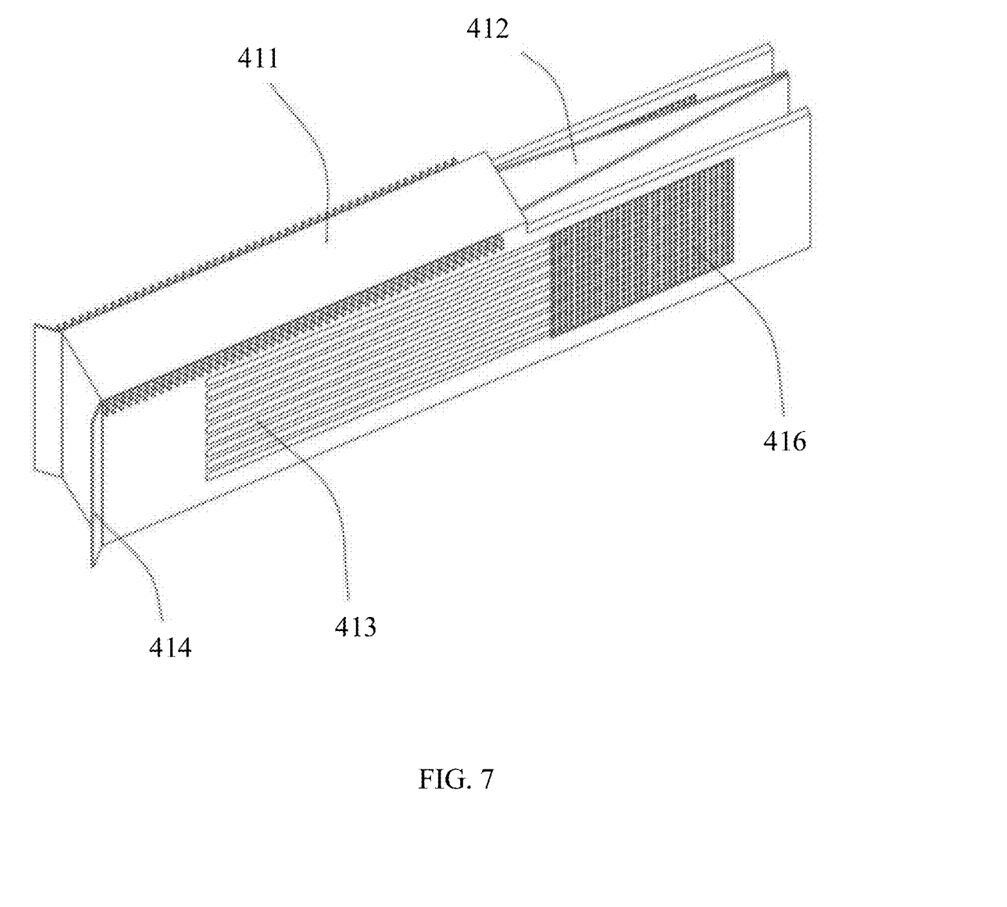
FIG. 7 is a structural sectional view of an air intake cover in the present invention.
Figure 8:
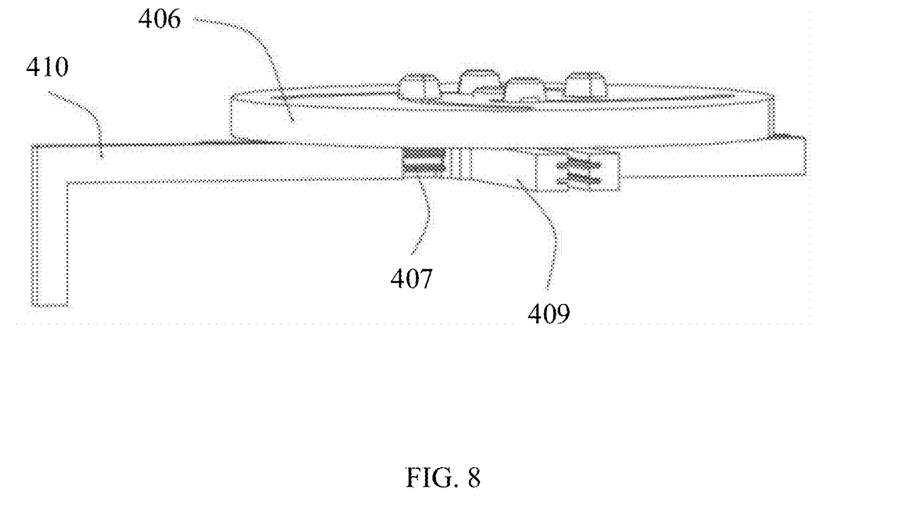
FIG. 8 is a structural schematic diagram of connecting parts, such as a rotating disk and an L-shaped frame in the present invention.

When the gas is in contact with each air intake cover 411, the wind direction is partially blocked through the baffle plate 414, and discharged to the position of the filter screen 416 along the diversion grooves 413. The diversion grooves 413 can help to guide the flow of wind and improve the collection efficiency of wind energy. Meanwhile, the air is discharged into each air intake cover 411 through the filter screen 416, and air impurities can be effectively reduced through the filter screen 416, thereby improving the accuracy of environmental monitoring data and further improving the use effect of the device. The air is discharged into the monitoring shell 2 along the air baffle plates 412. The air baffle plates 412 can increase the flow of the air and increase the entry of the air, to avoid air overflow, thereby further improving the use effect of the device and improving the monitoring effect.

In the process that each air intake cover 411 moves in the monitoring shell 2, each air intake cover 411 drives each second rack 501 to move synchronously. Because each second rack 501 is engaged with each second gear 502, each second gear 502 is driven to rotate. Through the rotation of each second gear 502, the chain mechanism 503 is driven to rotate. with the rotation of the chain mechanism 503, the cleaning rod 505 is driven to rotate. The impurities and dust on the surface of the filter screen 416 can be cleaned up through the cleaning rod 505 to avoid blocking the filter holes of the filter screen 416 by the dust and the impurities, thereby improving the smoothness of air entry, further improving the accuracy of air pollution monitoring data and ensuring the normal operation of the device. The structure is more flexible to use, thereby satisfying the actual use needs. On the other hand, the end grooves of the diversion grooves 413 can be cleaned to avoid blocking the ends of the diversion grooves 413, so as to improve the air intake effect.

When each air intake cover 411 moves in the monitoring shell 2, if the second magnet 607 corresponds to the first magnet 606, the second magnet 607 and the first magnet 606 produce magnetic adsorption through magnetism, and the U-shaped frame 605 is driven to move up. The U-shaped frame 605 drives each sealing plate 602 to slide on the surface of each limiting pin 603. As each sealing plate 602 moves up, the round holes are not sealed. At this time, the exhaust fans 601 are started. As the exhaust fans 601 are started, the residual air in the monitoring shell 2 is discharged from the monitoring shell 2. When the first magnet 606 is separated from the second magnet 607, then the magnetism disappears, and each sealing plate 602 is driven to move down through the rebound of the springs 604, to seal the round holes again. Then, the operation of the exhaust fans 601 is stopped. In this process, the previous air inside monitoring shell 2 is discharged, and new polluted air enters the monitoring shell 2 through each air intake cover 411, so that the air that remains inside the monitoring shell 2 is regularly discharged and new air is introduced, which can ensure that each detection is based on fresh air samples, thereby improving the accuracy and the reliability of the data. At the same time, by regularly discharging the residual air and introducing the new air, the dust accumulation inside the device can be reduced, and the risk of device failure can be reduced; and by regularly replacing the air samples, the wear inside the device can be slowed, thereby prolonging the service life of the device. The electric push rod 401 is started for resetting and driving each air intake cover 411 to move into the monitoring shell 2 near the position of the filter screen 416 to avoid air entry. Through the extension and contraction of each air intake cover 411 regularly, air is sampled, so as to prevent rainwater from intruding into the monitoring shell 2 and avoid affecting the service life of the electronic elements of the environmental monitor 3, thereby improving the use effect of the device and satisfying the actual use needs.

Finally, it should be noted that the above description is only a preferred embodiment of the present invention, and is not intended to limit the present invention. Although the present invention is described in detail with reference to the above embodiment, those skilled in the art may still modify the technical solution recorded in the above embodiment, or equivalently replace some of the technical features. Any modification, equivalent replacement, improvement, etc. made within the spirit and the principle of the present invention shall be included within the protection scope of the present invention.

What is claimed is:

1. An environmental monitoring device configured for air pollution, comprising a monitoring frame (1), a monitoring shell (2) arranged on a top end of the monitoring frame (1) and an environmental monitor (3) fixedly installed inside the monitoring shell (2) through a connecting plate;
   wherein an air sampling assembly (4) is installed above the environmental monitor (3); the air sampling assembly (4) comprises air intake covers (411), and an electric push rod (401), a first rack (402), a first gear (403), a spur gear (404), an internal gear (405), a rotating disk (406), limiting blocks (407), limiting rods (408), a cross-limiting track (409), an L-shaped frame (410) and a strip-shaped plate (417) which are used for driving the air intake covers (411); the cross-limiting track (409) is fixed inside the monitoring shell (2); the rotating disk (406) is rotatably connected to a center of an upper surface of the cross-limiting track (409) through a rotating shaft; four groups of limiting blocks (407) arranged annularly and equidistantly are slidably connected inside the cross-limiting track (409); the limiting rods (408) are fixed on upper surfaces of the limiting blocks (407); a surface of the rotating disk (406) is provided with limiting grooves adapted with the limiting rods (408); the internal gear (405) is fixed to an upper surface of the rotating disk (406); an inner side of the internal gear (405) is engaged with the spur gear (404); the rotating shaft is fixed at an inner center of the spur gear (404) through a screw; the first gear (403) is fixed to the surface of the rotating shaft; a surface of the first gear (403) is engaged with the first rack (402); the strip-shaped plate (417) is fixed to an inner side wall of the monitoring shell (2); an upper surface of the strip-shaped plate (417) is connected with the electric push rod (401) through a bolt; a top end of the rotating shaft is rotatably connected with the strip-shaped plate (417) through a bearing; the L-shaped frame (410) is fixed to one side of the limiting blocks (407); each air intake cover (411) is fixed to one end of the L-shaped frame (410); both sides of a surface of each air intake cover (411) are provided with air intake holes arranged symmetrically; and the air intake holes of the air intake covers (411) are fixedly connected with filter screens (416) through screws;
   wind blows the air intake covers (411) so that the air intake covers (411) drive the monitoring shell (2) to rotate on the monitoring frame (1);
   a cleaning assembly (5) is installed on the air sampling assembly (4); the cleaning assembly (5) comprises a cleaning rod (505) for cleaning dust of a filter screen (416), second racks (501), second gears (502), a chain mechanism (503) and a fixing plate (504); the symmetrically arranged second racks (501) are fixed to both sides of each air intake cover (411); surfaces of the second racks (501) are engaged with the second gears (502); first rotating rod is installed inside the second gears (502) through a screw; the chain mechanism (503) rotates on a top end of the first rotating rod; a second rotating rod rotates on one end of the chain mechanism (503); the cleaning rod (505) is fixed to a bottom end of the second rotating rod; the fixing plate (504) is fixed to one side of a surface of the monitoring shell (2) near the cleaning rod (505); and the fixing plate (504) is rotatably connected with the first rotating rod and the second rotating rod through bearings;

an exhaust assembly (6) is installed inside the monitoring shell (2); the exhaust assembly (6) comprises exhaust fans (601) configured for exhaust, sealing plates (602), limiting pins (603), a U-shaped frame (605), a first magnet (606) and second magnets (607);

round holes are arranged at bottom four corners of the monitoring shell (2); the exhaust fans (601) are arranged in the round holes; two groups of symmetrically arranged sealing plates (602) are installed inside the monitoring shell (2); limiting pins (603) are slidably connected inside the sealing plates (602) respectively; the U-shaped frame (605) is fixed to upper surfaces of two groups of the sealing plates (602) respectively; the first magnet (606) is fixed to an upper surface of the U-shaped frame (605); bottoms of four groups of the air intake covers (411) are provided with rectangular grooves; and the second magnets (607) are arranged in the rectangular grooves;

when each air intake cover (411) moves in the monitoring shell (2), if the second magnets (607) corresponds to the first magnet (606), the second magnets (607) and the first magnet (606) produce magnetic adsorption through magnetism, and the U-shaped frame (605) is driven to move up; the U-shaped frame (605) drives each sealing plate (602) to slide on the surface of the limiting pin (603); and as each sealing plate (602) moves up, the round holes are unsealed.

2. The environmental monitoring device configured for air pollution according to claim 1, wherein the surface of the monitoring shell (2) is provided with a moving groove adapted with each air intake cover (411), and each air intake cover (411) and the monitoring shell (2) are slidably connected through the moving groove.

3. The environmental monitoring device configured for air pollution according to claim 2, wherein two groups of air baffle plates (412) arranged symmetrically are fixed inside each air intake cover (411).

4. The environmental monitoring device configured for air pollution according to claim 3, wherein a plurality of groups of diversion grooves (413) arranged equidistantly are arranged on both sides of each air intake cover (411).

5. The environmental monitoring device configured for air pollution according to claim 4, wherein two groups of baffle plates (414) arranged symmetrically are fixed to one side of each air intake cover (411), and a supporting plate (415) is connected inside the monitoring shell (2) through a bolt.

6. The environmental monitoring device configured for air pollution according to claim 1, wherein a spring (604) is wound on the surface of each limiting pin (603).

* * * * *